United States Patent [19]
Duong-Van

[11] Patent Number: 5,456,690
[45] Date of Patent: Oct. 10, 1995

[54] SYSTEM AND METHOD FOR FRACTAL PULSE DEFIBRILLATION

[75] Inventor: Minn Duong-Van, Palo Alto, Calif.

[73] Assignee: Ventritex, Inc., Sunnyvale, Calif.

[21] Appl. No.: 137,382

[22] Filed: Oct. 14, 1993

Related U.S. Application Data

[63] Continuation-in-part of Ser. No. 65,203, May 20, 1993, abandoned.

[51] Int. Cl.⁶ ..................................................... A61N 1/39
[52] U.S. Cl. .................................................. 607/5; 607/73
[58] Field of Search ................................... 607/5, 70, 72, 607/73

[56] References Cited

U.S. PATENT DOCUMENTS

| 3,706,313 | 12/1972 | Milani et al. |
| 3,924,641 | 12/1972 | Weiss |
| 4,637,397 | 12/1972 | Jones et al. |
| 4,706,313 | 12/1972 | Milani et al. |
| 4,708,145 | 11/1987 | Tacker, Jr. et al. |
| 4,768,512 | 9/1988 | Imran |
| 4,850,357 | 7/1989 | Bach, Jr. |
| 4,998,531 | 3/1991 | Bocchi et al. |
| 5,048,521 | 9/1991 | Pless et al. |
| 5,107,834 | 4/1992 | Ideker et al. ................................. 607/5 |

OTHER PUBLICATIONS

"Experimental Control of Choas", W. L. Ditto, Physical Review Letters, Dec. 24, 1990.
"Controlling Cardiac Chaos" (Garfinkel, et al), Science, vol. 257, (Aug. 28, 1992).
"Controlling Chaos" (Ott, et al) American Review Letters, vol. 64, No. 11 (Mar. 12, 1990).
"Experimental Control of Chaos" (Ditto, et al) Physical Review Letters, vol. 65, No. 26 (Dec. 24, 1990).
"Method of Controlling Chaos in Laser Equations"(Duong-van) Physical Review E, vol. 47, No. 1 (Jan. 1993).
"Crazy Rhythms-Confronting the Complexity of Chaos in Biological Systems" (Peterson, et al) Science News, vol. 142 (Sep. 5, 1992).
"Nonlinear Dynamics, Chaos and Complex Cardiac Arrhythmias" (Glass, et al).
"Fascinating Rhythm: A Primer on Chaos Theory and its Application to Cardiology" (Denton et al) American Heart Journal, vol. 120, No. 6, Part I, (Dec. 1990).

Primary Examiner—William E. Kamm
Assistant Examiner—Scott M. Getzow
Attorney, Agent, or Firm—Steven M. Mitchell; Mark J. Meltzer

[57] ABSTRACT

The present invention provides a system and method for delivering a defibrillation waveform which is a fractal or multifractal pulse sequence. In one embodiment of the invention, a plurality of monophasic rectangular or truncated exponential pulses are delivered with fractal timing. Each subsequent pulse in the sequence has a lower voltage than the preceding pulse and the pulses have equal duration. This fractal pulse sequence is generated in response to a sensed arrhythmia and it is delivered using conventional leads to a patient's heart. A predetermined fractal pulse sequence is stored in programmable memory and may be modified by a patient's physician.

13 Claims, 4 Drawing Sheets

SYSTEM AND METHOD FOR FRACTAL PULSE DEFIBRILLATION

This is a continuation-in-part of application Ser. No. 08/065,203 filed on May 20, 1993, now abandoned.

FIELD OF THE INVENTION

The present invention relates generally to implantable cardiac stimulation devices, and more specifically to a system and method for using fractal and multifractal defibrillation pulse sequences.

BACKGROUND OF THE INVENTION

A number of different systems and methods have been developed for delivering electrical shocks to a patient's heart in response to detected abnormal heart rhythms (arrhythmias). These methods deliver specific waveform shapes or pulse sequences to the heart in order to treat the detected arrhythmia. One early waveform is disclosed in U.S. Pat. No. 3,706,313 to Milani et. al., which provides a circuit for delivering a "trapezoidal" wave shape for defibrillating the heart by truncating the output of an exponentially decaying capacitor. Others have suggested the use of sequential pulses delivered through multiple pathways such as described in U.S. Pat. No. 4,708,145 to Tacker, Jr. In Tacker, Jr., a series of rectangular or truncated exponential pulses are delivered to the heart using at least three electrodes where a first pulse is sent through a first pair of the three electrodes and then a second pulse is sent through a second different pair of the electrodes. Still others have described the use of multiphasic waveforms such as U.S. Pat. No. 4,637,397 to Jones et. al. which describes a triphasic waveform. A triphasic waveform has three pulses of alternating positive and negative polarity. U.S. Pat. No. 3,924,641 to Weiss and U.S. Pat. No. 4,850,357 to Bach, Jr. describe the use of biphasic waveforms. These defibrillation pulses are typically in the range of from 500 to 1000 volts delivered for a time of from about 2 to 10 msec. Overall energy delivery for a defibrillation waveform may typically be from about 10 to 30 joules.

There has been much debate over the optimum waveform, i.e. which waveform is most effective from a therapeutic standpoint and also most efficient from an energy delivery standpoint. The primary goal in treating a detected fibrillation with an implantable cardioverter/defibrillator is to minimize energy delivery requirements for the defibrillation waveform by providing the most effective therapy with the lowest energy. Lower voltage shocks are less painful and disruptive to the patient and lower energy requirements allow for use of smaller batteries and capacitors and thus smaller implantable devices.

A modification of the standard waveform has been suggested by Imran in U.S. Pat. No. 4,768,512. That patent discloses a cardioverting system (defibrillation and cardioversion) in which a truncated exponential waveform is chopped at high frequencies to provide a voltage wave packet formed of a plurality of high-frequency cardioverting pulses with a preferred frequency in excess of 1 KHz. Iraran teaches that different heart tissues have different impedances at different frequencies and that tissues of high and low impedance are distributed throughout the heart. Thus, with high-frequency pulses, the energy is distributed throughout the heart resulting in lower energy requirements for effective cardioversion.

The electrical activity of the heart reflects the activity of a dynamical system. A dynamical system is a system which may be described with differential equations having at least three independent dynamical (time dependent) variables and the equations must contain a nonlinear term which couples several of the variables. This coupling is a manifestation of feedback. Dynamical systems such as the heart can exhibit both periodic and chaotic behavior depending on certain system parameters. These parameters appear as constants in the differential equations describing the system. The chaos exhibited by the heart may not be immediately obvious by looking at an ECG. One standard way of observing the chaotic behavior of the heart has been to plot the interbeat spacing at time n against the interbeat spacing at time n+1. Such a plot is known as a Poincaré map or return map. However, it has been discovered that a better variable for representing the dynamical system of the heart is the amplitude of the ECG. FIG. 1A shows such a plot for a human heart as it goes from a normal heart rhythm to the transition to the chaos of fibrillation. The plot covers about 8 seconds with 4000 data points each taken at 2 milliseconds apart. For the particular ECG of this example, the delay time for the return map has been found to be 088 seconds or 44 data points. Thus, the figure shows the amplitude of the ECG at time n plotted against the amplitude at time n+44. The plot shows a pattern with a high degree of organization for normal heart rhythm until the transition to chaos. FIG. 1B shows a continuation of about 4 seconds of the plot for the ECG used in FIG. 1A as the heart is fibrillating, clearly exhibiting chaotic behavior. This technique of viewing the heart dynamical system can thus provide an improved mechanism for interpreting the behavior of the heart.

It has been shown that a chaotic system can be controlled by continuously applying proportional feedback to the system. This technique has been described with respect to laser systems in "Method of controlling chaos in laser equations", Phys. Rev. E, Minh Duong-van, Vol. 47, No. 1, pp. 714–717, Jan. 1993. This type of continuous control for treating cardiac arrhythmias has been proposed by Garfinkel et. al. in SCIENCE Vol. 257, pp. 1230–1235, 28 Aug. 1992. However, the proposed technique may be undesirable because it requires continuous therapy. If the therapy is discontinued, the heart returns to fibrillation.

It is an object of the present invention to provide an improved o defibrillation waveform which allows effective therapy with lower energy delivery requirements.

It is a further object of the invention to utilize the chaotic behavior of the heart system to provide a more efficient defibrillation therapy.

SUMMARY OF THE INVENTION

The present invention provides a system and method for delivering a defibrillation therapy which comprises a fractal or multifractal electrical pulse sequence. The inventor has discovered that by using the same equations which describe the chaotic behavior of lasers and the calcium-potassium-sodium channels of the thyroid-pituitary system, fibrillation can be controlled by momentary feedback rather than continuous feedback. In one embodiment of the invention, a plurality of monophasic rectangular or truncated exponential pulses are delivered with fractal timing. Each subsequent pulse in the sequence has a lower voltage than the preceding pulse and the pulses have equal duration. This fractal pulse sequence is generated in response to a sensed fibrillation and it is delivered using conventional leads connected to a patient's heart. In the system of the preferred embodiment of the invention, a RAM memory is provided for storing a predetermined fractal pulse sequence. The memory is externally programmable by a patient's physician.

BRIEF DESCRIPTION OF THE DRAWINGS

The various features and advantages of the present invention may be more readily understood with reference to the following detailed description taken in conjunction with the accompanying drawings in which.

DETAILED DESCRIPTION OF THE INVENTION

Figure 1A:
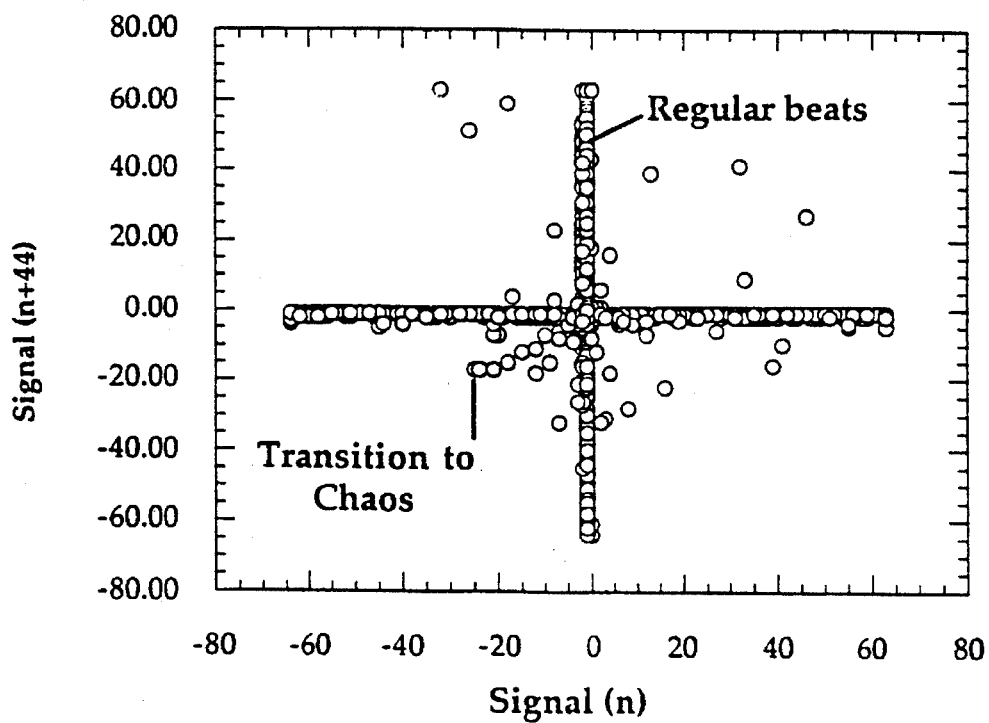
FIGS. 1A and 1B show plots of an exemplary Poincaré map of ECG amplitude for a normal heart rhythm and its transition to fibrillation and of the same ECG with the heart in fibrillation.
Figure 1B:
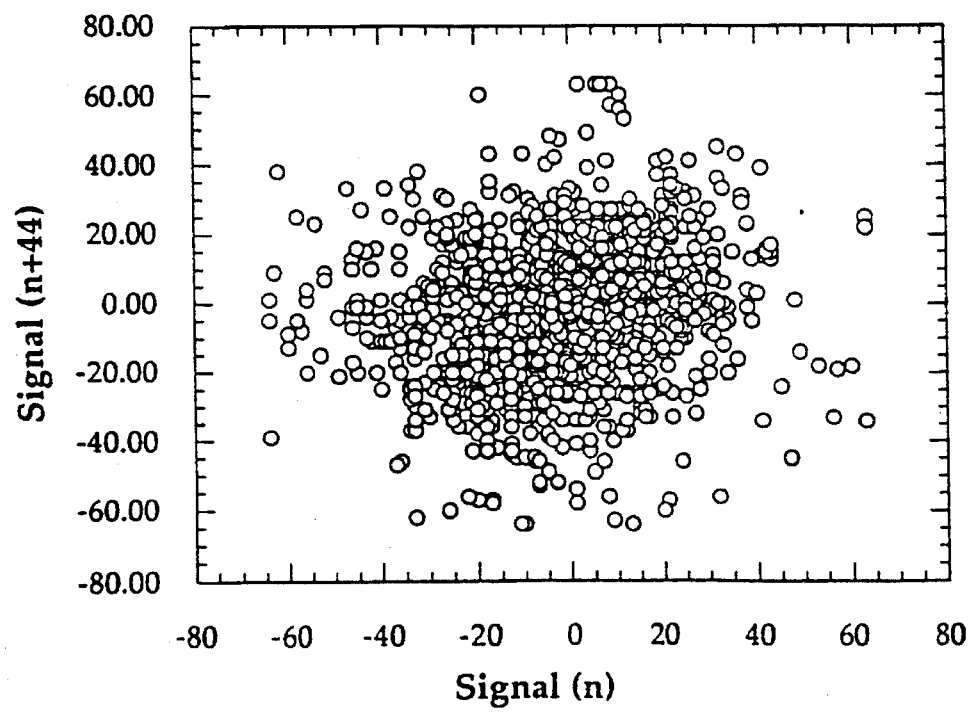
Figure 2:
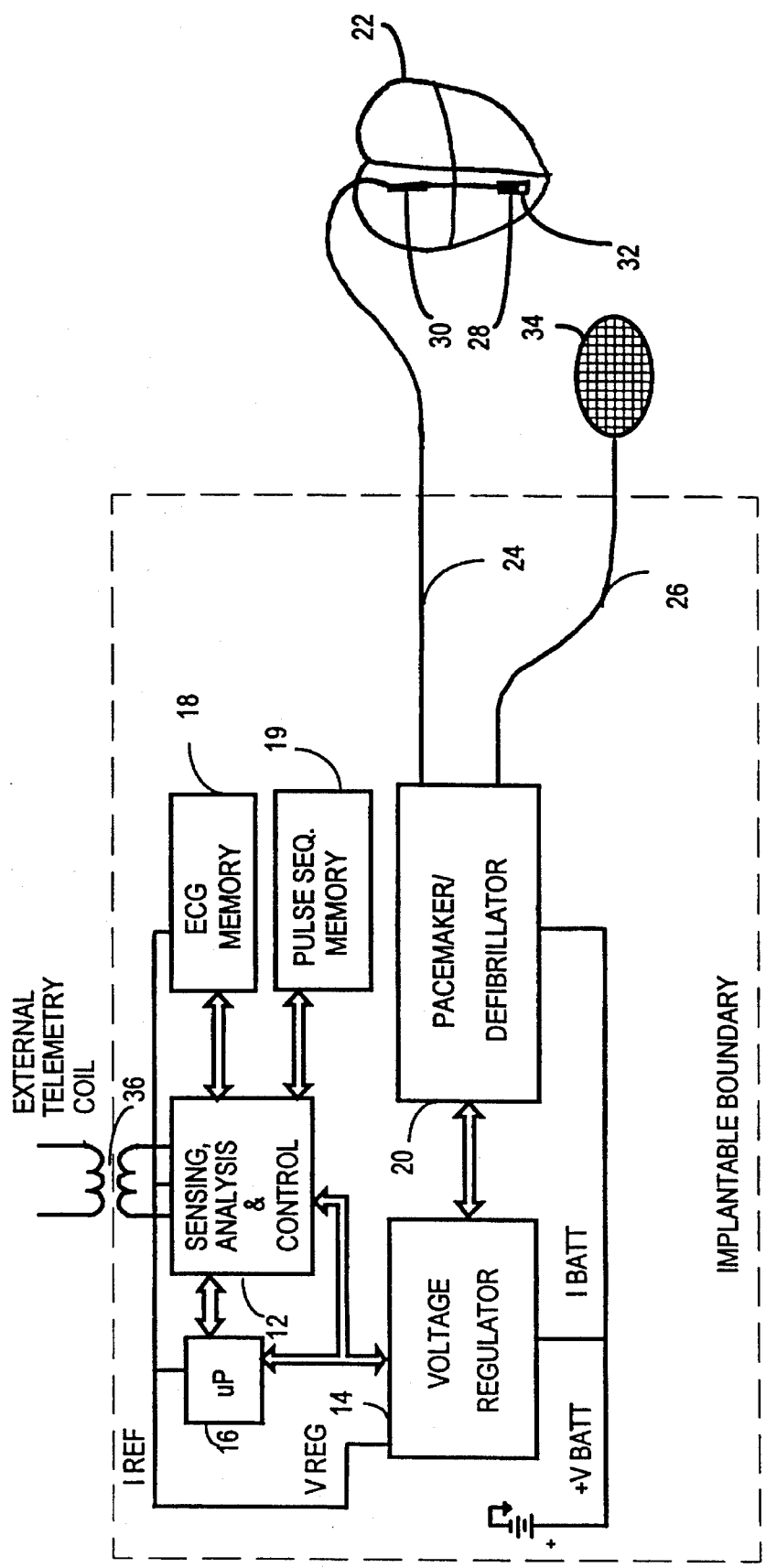
FIG. 2 is a block diagram illustrating the cardioverter/defibrillator system of the invention.

The system of the invention will now be discussed with reference to FIG. 2 which provides a block diagram showing the general organization of an implantable cardioverter/defibrillator system 10. In addition to providing defibrillation pulses in a preferred embodiment of the invention, the system is also capable of providing tachyarrhythmia and Bradycardia therapy. The system 10 includes sensing, analysis and control circuitry 12, a voltage regulator circuit 14 and an 8-bit microprocessor 16. A first static RAM 18 is used to store digitized ECG waveforms. A second static RAM 19 is used to store defibrillation waveforms. A first external connection from pacemaker/defibrillator circuitry 20 to the patient's heart 22 is provided by lead 24 which is provided with an SVC electrode 30, an RV electrode 28 and a pacing/sensing tip 32. A second external connection from the pacemaker/defibrillator circuitry 20 is provided by lead 26 which is connected to subcutaneous patch electrode 34. The pacing/sensing tip 32 provides millivolt level ECG signals through lead 24 which also carries pacing pulses from the pacemaker/defibrillator 20 to the heart 22. Telemetry to and from an external programmer (not shown) is carried via a coil-to-coil link 36. System software decides whether the ECG parameters indicate an arrhythmia and, if so, the appropriate therapy in accordance with the invention is initiated. The raw ECG data can also be stored in memory 18 for later retrieval or be telemetered out of the system 10 in real time. The sensing, analysis & control circuitry 12 communicates with programmable RAM memory 19 which is used to provide the irregular or fractal pulse sequence for defibrillation therapy as is described below. The memory may be modified by the external programmer to provide the number of pulses, the voltage and width of each pulse and the spacing (timing) between the pulses. As an alternative to the externally programmed pulse sequence, the sensing, analysis and control circuitry can include an algorithm which generates appropriate fractal pulse sequences.

Since the heart is a dynamical system and it's behavior has been observed to correspond to other dynamical systems such as lasers and laminar flow in a fluid system, the heart can be described using the Lorenz-Laser equations in dimensionless form:

$$(d/dt+a)x=ay \tag{1}$$

$$(d/dt+1)y=-xz \tag{2}$$

$$(d/dt+1)z=xy-R \tag{3}$$

These equations can be used to model the chaotic functioning of the heart and to derive a more effective defibrillation control scheme. Control of the system may be achieved by adding a control term which represents a series of electrical pulses. With the control term, equation (3) above becomes:

$$(d/dt+1)z=xy-R-\epsilon\Sigma\Pi^{bc}(\tau,x^2) \tag{4}$$

where $\Pi$ is a function which is a series of pulses having frequency $\tau$, width from time b to time c, and pulse height x. Appendix A provides a computer program for simulating the heart dynamical system and which can be used to identify an effective control scheme. R is the driving term and is 50 in the model. The feedback term, $\epsilon$, is equal to 1.975 which is considered to provide strong feedback and thus represents a relatively high degree of system stability. The timer term represented by the function $\Pi$ is alternatingly on for 14 units and off for 16 units. For the model, the time unit is one one thousandth (1/1000) of an average beat interval of ¾ of a second. Thus, each unit dt in the model is ¾ milliseconds. The reason for selecting these units for the model rather than having dt tend toward zero as is normally done to simulate mathematical integration is that we are working with a physical system which has a limited response time.

Understanding of the proper control scheme to control fibrillation is further influenced by the observation that fibrillation can be considered as intermittency chaos. Chaos is a state of the dynamical system where the system dwells chaotically between two attractors. The degree of chaoticness can be near chaos, or far chaos depending on whether the parameter is close to or far from steady or periodic solutions. Intermittency chaos is a state where the system is very close to regular oscillation and it can be simply perturbed to go back to regular oscillation. Thus, although the signal may appear disturbingly erratic in the intermittency chaos state, it can easily be brought back to periodicity. This is the basis for the control scheme used in equation (4).

As mentioned before, the heart system appears to have two attractors as is true for many well known dynamical systems. When a normal rhythm is present, the heart dwells at or near one of the two attractors. When the heart experiences fibrillation, the presence of the other attractor appears. The control scheme of the invention is designed to push the system back toward the one attractor where the system exhibits normal rhythm. This can be done in one of two ways. First, the system parameters can be modified. These parameters for the heart system are the constants "a" and "R" in equations (1) and (3) above. In the case of a laser system, "a" represents the life time of the atoms and "R" represents the pump term. Unlike the case of the laser system where "R" can be changed at will, in the case of the heart changing these parameters is difficult since they are not clearly identified even though they have been modeled from experimental data. Also, they may be difficult to modify on an effective time scale. The second way to control the system is to modify the system variables. This is accomplished by resetting the value of the electrical signals of the heart by electric pulsing. This is effective because of the feature of dynamical systems of sensitivity to initial conditions. Thus, the prior art control schemes of delivering electrical pulses to the heart are actually resetting the system variables for the Lorenz equations of the heart dynamical system. To achieve this, the chaotic attractor must be identified and quantified. Then the information of the attractor can be used to defibrillate the heart. In the past, optimization of the pulsing has not been approached from the standpoint of looking at the nature of the attractor of the fibrillating heart in developing a mechanism for defibrillation.

Figure 3A:
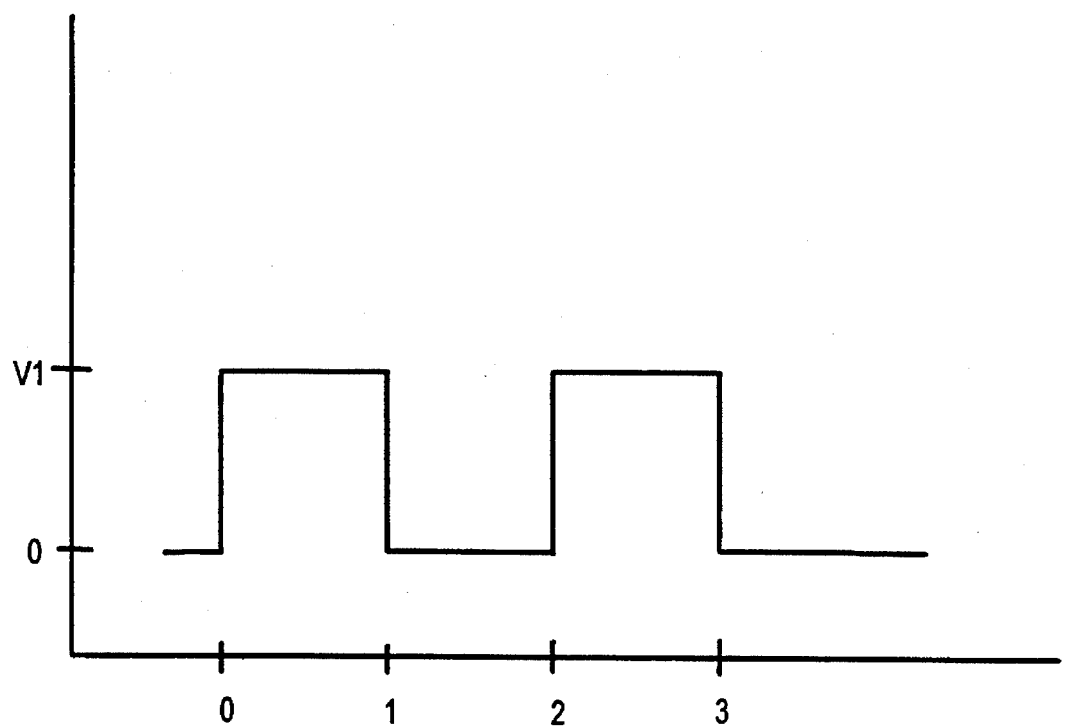
FIG. 3A shows a first generation of a Cantor set used to produce a fractal pulse sequence.
Figure 3B:
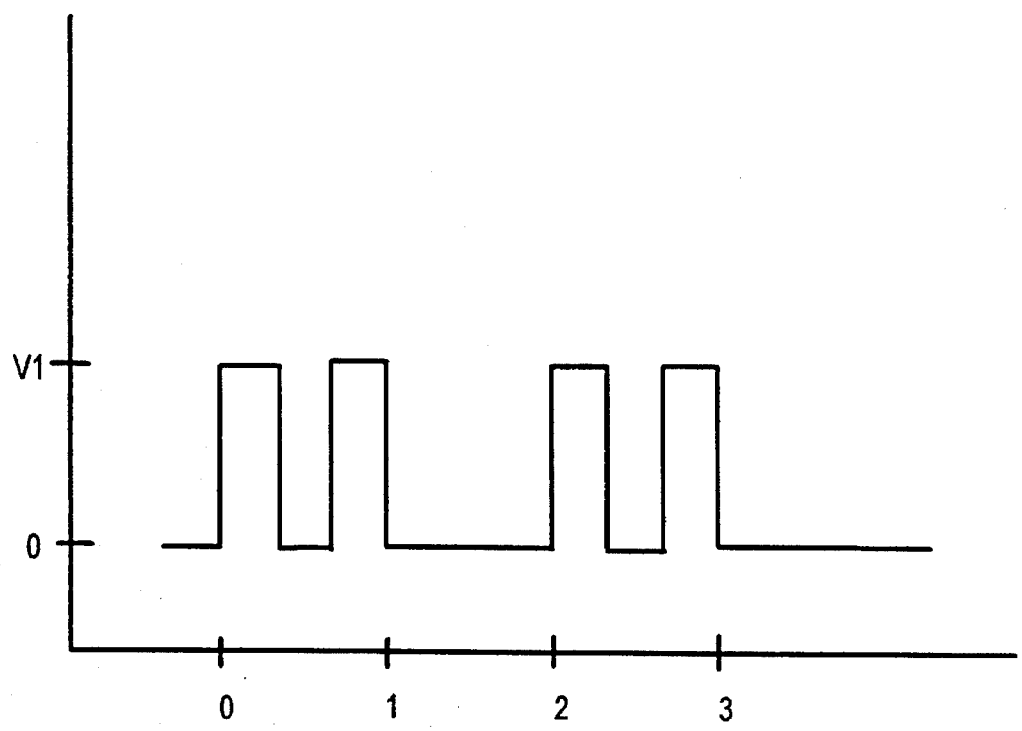
FIG. 3B shows a second generation of the Cantor set fractal pulse sequence of FIG. 3A.

The present invention has been derived by using the modeling described above and applying various pulsing schemes to optimize chaos control. The method of the invention involves delivering an irregular or fractal pulse sequence to defibrillate the heart. An example of a fractal pulse sequence can be demonstrated with the simplest fractal. This is the well known ternary Cantor set. If the monophasic defibrillation pulse is considered as a time segment, the time segment is divided into three equal parts of unit length. For the first iteration of the fractal, the middle third of the time segment is thrown out resulting in a waveform as shown in FIG. 3A, leaving two non-empty elements. Thus, a first pulse having a voltage $V_1$ is generated for the first non-empty element and then is turned off for the next empty element and then turned back on for the final non-empty element. The waveform comprises two equal length pulses separated by a time gap of the same length. For the second iteration, the remaining two non-empty elements are further divided according to the same rule: divide each segment into three equal parts, then throw away the middle third. For this embodiment two small segments of length ⅓ are separated by a time gap of unit length from two more small segments of length ⅓ separated from each other by a segment of length ⅓ as illustrated in FIG. 3B. In this second generation, the fractal waveform consists of four pulses. This process can be continued depending on the level of control required. A multifractal is a generalization of the fractal. The time segment may be divided in more than three parts and more than one part of any length can be thrown away. As used herein, fractal is intended to cover both fractal and multifractal pulse sequences.

Figure 4A:
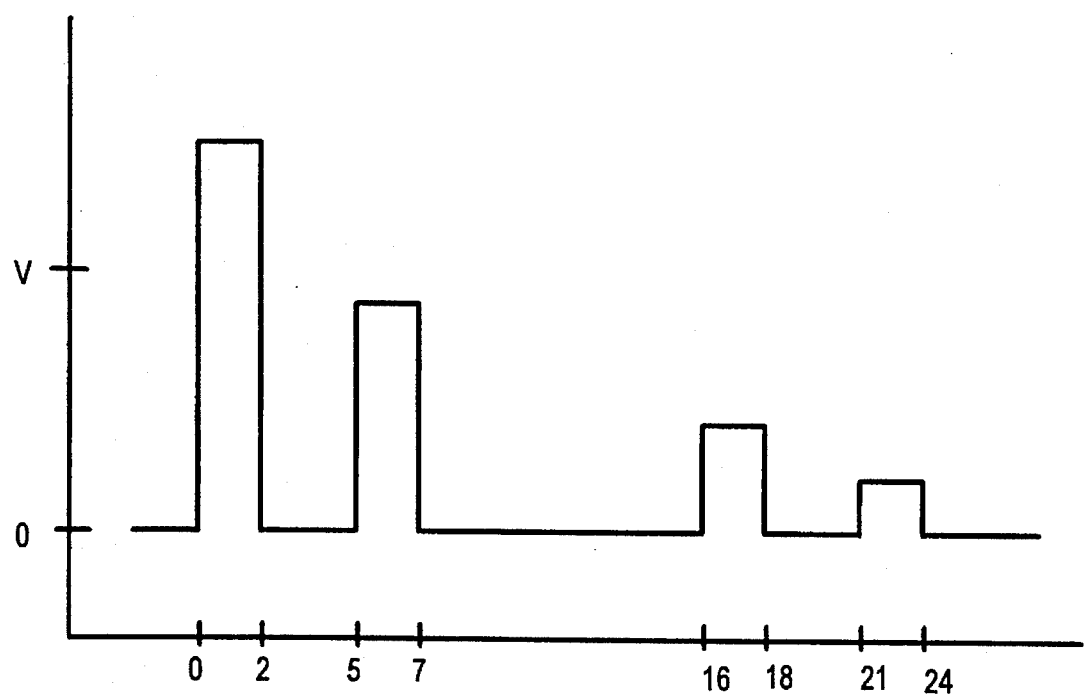
FIG. 4A shows a fractal pulse sequence with rectangular pulses used in a preferred embodiment of the invention.
Figure 4B:
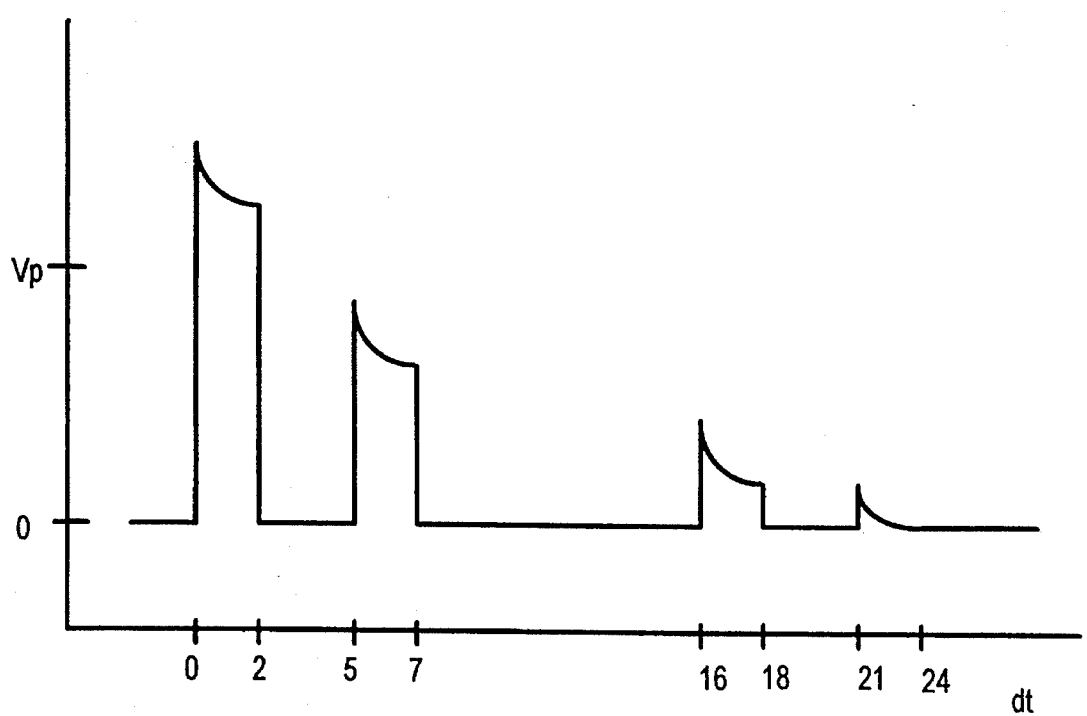
FIG. 4B shows a fractal pulse sequence with truncated exponential pulses used in another preferred embodiment of the invention.

In the preferred embodiment of the invention, a modified Cantor set is used to create a fractal pulse sequence as shown in FIGS. 4A and 4B. First, the spacing between pulses has been modified. The timing of the pulses is that each pulse has a width of 2dt or 1.5 msec, the spacing between the trailing edge of the first and third pulses and the leading edges of the second and fourth pulses, respectively, is 3dt or 2.3 msec and the time between the trailing edge of the second pulse and the leading edge of the third pulse is 9dt or 6.75 msec. It will be understood that the choice of dt is dependent on the structure of the attractor of the heart dynamical system. Next, each subsequent pulse after the first pulse of the sequence has a lower voltage than the preceding pulse. Thus, the pulse sequence can be delivered using the exponentially decaying voltage of a single capacitor or capacitor bank as shown in FIG. 4B. If "$V_p$" is considered the unit of pulse strength, the relative values of the pulses in the sequence is $1.5V_p$ for the first pulse, $0.9V_p$ for the second pulse, $0.4V_p$ for the third pulse, and $0.2V_p$ for the fourth pulse. Each subsequent pulse after the first pulse of the sequence has a lower voltage than the preceding pulse.

It should be understood that various alternatives to the embodiments of the invention described herein may be employed in practicing the invention. For example, the system and method of the invention can be used in an external defibrillator. It is thus intended that the following claims define the scope of the invention and that structures and methods within the scope of these claims and their equivalents be covered thereby.

Appendix A

```
dimension z(100000)
character*3 ff
j = 0
do 3 k=1,1
sh=20.07499897+.002*(k-1)
j = j+1
ff = 'aa'//char(j+48)
write(*,*)ff
open(unit=5,file=ff,status='unknown')
x1=2.5482
y1=8.339854
z(1)=1.523974
dt=.00248
pr=10.
r=50.
np=60000
mm=100
iw=14
it=30
eps=1.975
ca=pr=10 r=50 14-30 eps=1.975 dt=.0025 get the healing
c as in alordriven oct-4-92
do 100 i=2,np
ispace=int(i/it)
idiff=i-it*ispace
if (idiff.gt.iw) then
ifb = 0
else
ifb = 1
endif
x= x1+ dt*pr* (y1 - x1)
y= y1+ dt*(-x1*z(i-1) - y1)
z(i)=z(i-1) + dt*(-r-eps*ifb*x1**2-z(i-1)+x1*y1)
if(i.gt.20000. and. i.lt.20002) then
z(i)=z(i)+sh*1.5
endif
if(i.gt.20003. and. i.lt.20004) then
z(i)=z(i)+0.
endif
if(i.gt.20005. and. i.lt.20007) then
z(i)=z(i)+sh*.9
endif
if(i.gt.20008. and. i.lt.20015) then
z(i)=z(i)+0.
endif
if(i.gt.20016. and. i.lt.20018) then
z(i)=z(i)+sh*.4
endif
if(i.gt.20019. and. i.lt.20020) then
z(i)=z(i)+0.
endif
if(i.gt.20021. and. i.lt.20023) then
z(i)=z(i)+sh*.2
endif
is=int(i/mm)
if (i-mm*is.eq.0) then
write(5,33) i,char(9),x
format(i10,a1,f10.2)
endif
x1=x
y1=y
continue
continue
stop
end
```

What is claimed is:

1. An implantable pulse generation system for treating an arrhythmic heart condition comprising:

means for sensing the heart condition;

energy storage means;

means for charging said energy storage means;

means for discharging said energy storage means;

a pair of implantable electrodes coupled to said energy storage means for delivering energy pulses to a patient's heart; and control means coupled to said means for discharging for generating an irregular pulse sequence and delivering said sequence though said pair of electrodes in response to a sensed heart condition.

2. The system of claim 1 said irregular pulse sequence is a fractal pulse sequence.

3. The system of claim 1 and further including programmable memory means coupled to said control means for storing a predetermined irregular pulse sequence.

4. A method of treating a heart arrhythmia using an implantable cardioverter/defibrillator comprising the steps of:

sensing an arrhythmia condition;

charging an energy storage means;

delivering a fractal pulse sequence from said energy storage means to the heart through a pair of electrodes.

5. The method of claim 4 wherein each of said pulses has substantially the same duration.

6. The method of claim 4 wherein each subsequent pulse after an initial pulse of said pulse sequence is delivered at a lower voltage than the preceding pulse.

7. The method of claim 6 wherein each of said pulses is a truncated exponential pulse.

8. The method of claim 7 wherein each of said pulses has the same duration.

9. A method of controlling ventricular fibrillation or tachycardia in a patient's heart using a defibrillator comprising the steps of sensing an arrhythmia condition and delivering a fractal sequence of energy pulses to the heart from a pair of electrodes.

10. The method of claim 9 and further including the step of charging an energy storage means prior to delivering said pulses.

11. A pulse generation system for treating an arrhythmic heart condition comprising:

energy storage means;

energy delivery means including a pair of electrodes; and control means coupled to said energy delivery means for generating a fractal pulse sequence for delivery through said pair of electrodes.

12. The system of claim 11 and further including means for sensing the heart condition.

13. The system of claim 12 wherein said system is adapted for implantation into a patient's body, said system further including a pair of implantable electrodes coupled to said energy delivery means for delivering said pulse sequence to the patient's heart.

* * * * *